United States Patent
Miyajima et al.

[11] Patent Number: 5,891,450
[45] Date of Patent: Apr. 6, 1999

[54] POLYSACCHARIDE DERIVATIVE, AND PREPARATION PROCESS AND USE THEREOF

[75] Inventors: Tetsuya Miyajima; Tomohito Kitsuki; Katsumi Kita; Hiroshi Kamitani, all of Wakayama; Kazuhiro Yamaki, Tokyo, all of Japan

[73] Assignee: Kao Corporation, Tokyo, Japan

[21] Appl. No.: 773,533

[22] Filed: Dec. 23, 1996

[30] Foreign Application Priority Data

Dec. 27, 1995 [JP] Japan .................................. 7-341012
May 9, 1996 [JP] Japan .................................. 8-114860

[51] Int. Cl.$^6$ ................................................. A61K 7/48
[52] U.S. Cl. ........................... 424/401; 424/59; 424/64; 424/69; 424/78.02; 514/56; 514/844; 514/937; 536/55.1; 536/123.1
[58] Field of Search .............................. 424/401, 59, 64, 424/69, 78.02; 536/56, 102, 90, 91, 92, 55.1, 123.1; 514/56, 844, 937

[56] References Cited

U.S. PATENT DOCUMENTS

| | | | |
|---|---|---|---|
| 3,435,027 | 3/1969 | Desmarais et al. | 260/226 |
| 5,177,199 | 1/1993 | Kiesewetter et al. | 536/90 |
| 5,182,380 | 1/1993 | Breckwoldt et al. | 536/90 |
| 5,278,304 | 1/1994 | Kniewske et al. | 536/90 |

FOREIGN PATENT DOCUMENTS

| | | |
|---|---|---|
| 0 471 866 | 2/1992 | European Pat. Off. . |
| 0 554 751 | 8/1993 | European Pat. Off. . |

OTHER PUBLICATIONS

JP 55110103 Abstract 1980 English Language Abstracts Only Provided.
JP 56000801 Abstract 1981 English Language Abstracts Only Provided.
J0 3012401 Abstract 1991 English Language Abstracts Only Provided.
JP 03141210 Abstract 1991 English Language Abstracts Only Provided.
JP 03141214 Abstract 1991 English Language Abstracts Only Provided.
JP 03218316 Abstract 1991 English Language Abstracts Only Provided.
J 02212579 Abstract 1990 English Language Abstracts Only Provided.
JP 03220153 Abstract 1991 English Language Abstracts Only Provided.
JP 94228023 Abstract 1994 English Language Abstracts Only Provided.
JP 5624401 Abstract (Mar. 09,1981).
JP 6318203 Abstact (Jul. 27.1988).

*Primary Examiner*—Jyothsna Venkat
*Attorney, Agent, or Firm*—Oblon, Spivak, McClelland, Maier & Neustadt, P.C.

[57] ABSTRACT

Disclosed herein are a polysaccharide derivative obtainable by substituting a part or the whole of hydrogen atoms of hydroxyl groups in a polysaccharide or a derivative thereof by the following substituents (A) and (B):

(A) a hydrophobic group containing a $C_{10}$–$C_{40}$ alkyl, alkenyl or acyl group which may be substituted by an —OH group or into which an oxycarbonyl group (—COO— or —OCO—) may be introduced; and (B) a $C_1$–$C_5$ sulfoalkyl group which may be substituted by an —OH group, or a salt thereof, wherein average degrees of substitution by the substituents (A) and (B) per monosaccharide residue are 0.001–1.0 and 0.01–2.0, respectively; a preparation process thereof; and use of the polysaccharide derivative for a thickener for cosmetic compositions.

9 Claims, No Drawings

POLYSACCHARIDE DERIVATIVE, AND PREPARATION PROCESS AND USE THEREOF

BACKGROUND OF THE INVENTION

1. Field of the Invention

The present invention relates to a novel polysaccharide derivative, and more particularly to a novel polysaccharide derivative which has excellent transparency when dissolved in water, exhibits excellent thickening ability at a low concentration, undergoes little change in viscosity of its aqueous solution even either in coexistence with metal salts or by temperature changes and moreover shows extremely good emulsion stabilizing ability, a preparation process thereof, use of the polysaccharide derivative for a thickener for cosmetic compositions, and cosmetic compositions containing the same.

2. Description of the Background Art

Various cellulose ethers are widely used as one of important ingredients of cosmetics, toiletries, medicines for external application, water-soluble paints and the like, and as a thickener, gelling agent, excipient, emulsion stabilizer and/or flocculant. As such cellulose ethers, water-soluble nonionic cellulose ethers such as methyl cellulose, ethyl cellulose, hydroxyethyl cellulose, hydroxypropyl cellulose, hydroxypropylmethyl cellulose and ethylhydroxyethyl cellulose, ionic cellulose ethers such as carboxymethyl cellulose, cationized cellulose and cationized hydroxyethyl cellulose, and the like are commercially available and in use.

These cellulose ethers are relatively excellent in viscosity stabilizing ability for aqueous solutions in systems coexistent with inorganic metal salts or organic metal salts compared with polyacrylic acid type thickeners such as Carbopol, but are lower in thickening ability at the same concentration in an aqueous solution as the above thickeners. Therefore, it has been necessary to increase the amount of the cellulose ethers to be used to sufficiently exhibit their properties when used as a thickener or emulsion stabilizer for, in particular, cosmetics, toiletries and the like. However, the incorporation of the cellulose ethers in a great amount has caused problems from the viewpoint of feel such as a sticky feel and a filmy feel and has been accompanied by a drawback that the resulting product undergoes a great change by temperature changes and is hence difficult to be maintained in a stable form.

On the other hand, for example, Japanese Patent Application Laid-Open Nos. 110103/1980 and 801/1981 disclose that a hydrophobized nonionic cellulose derivative obtained by partially introducing a long-chain alkyl group having 10–24 carbon atoms into a nonionic water-soluble cellulose ether exhibits comparatively high thickening ability when mixed in a small amount with water. As found in Japanese Patent Application Laid-Open Nos. 12401/1991, 141210/1991, 141214/1991 and 218316/1991, an attempt has also been made to apply these alkyl-substituted cellulose derivatives to medicines for external application, cosmetic compositions and the like. However, these alkyl-substituted cellulose derivatives have excellent thickening ability compared with the cellulose ethers, but are poor in water solubility, and have hence involved such problems that it takes a long period of time to be evenly dissolved upon incorporation into a product, and they are poor in viscosity stability with time.

An ideal thickener to be used in cosmetics and toiletries requires that it is easily dissolved to exhibit an excellent thickening effect, the viscosity of its solution is scarcely affected by metal salts, surfactants, oily substances and other additives coexistent therewith, changes in temperature and pH, such a solution scarcely undergoes a change in viscosity with time, and it gives users a pleasant feeling upon use without being sticky to the touch and has excellent microbial resistance. However, the cellulose ethers and alkyl-substituted cellulose derivatives have not fully satisfied all of these performance characteristics required.

SUMMARY OF THE INVENTION

It is accordingly an object of the present invention to provide a novel polysaccharide derivative which exhibits high thickening ability at a low concentration, can provide a solution the viscosity of which is hard to be affected by inorganic metal salts, organic metal salts, temperature, pH and the like, gives users a pleasant feeling upon use when used in cosmetics and toiletries, and shows excellent thickening ability and emulsion stabilizing ability, a preparation process thereof, and cosmetic compositions containing the same.

In view of the foregoing circumstances, the present inventors have carried out an extensive investigation. As a result, it has been found that a novel polysaccharide derivative obtainable by substituting hydrogen atoms of hydroxyl groups in a polysaccharide by a specific hydrophobic substituent and a substituent containing a sulfonic group is excellent in water solubility, exhibits high thickening ability at a low concentration in an aqueous solution, is hard to be affected by inorganic metal salts, organic metal salts, pH, temperature and the like to stably exhibit the thickening ability, shows excellent emulsion stabilizing ability, and gives users a pleasant feeling upon use when used in cosmetics and toiletries, thus leading to completion of the present invention.

According to the present invention, there is thus provided a polysaccharide derivative obtainable by substituting a part or the whole of hydrogen atoms of hydroxyl groups in a polysaccharide or a derivative thereof by the following substituents (A) and (B):

(A) a hydrophobic group containing a linear or branched alkyl, alkenyl or acyl group having 10–40 carbon atoms; and (B) a sulfoalkyl group having 1–5 carbon atoms, which may be substituted by a hydroxyl group, or a salt thereof, wherein an average degree of substitution by the substituent (A) per monosaccharide residue is 0.001–1.0, and an average degree of substitution by the substituent (B) per monosaccharide residue is 0.01–2.0.

According to the present invention, there is also provided a process for preparing a polysaccharide derivative by reacting a polysaccharide or a derivative thereof, either by stages or at the same time, with (a) a compound selected from the group consisting of glycidyl ethers, epoxides, halides, halohydrins, esters, acid anhydrides and acyl halides each having a hydrophobic group containing a linear or branched alkyl, alkenyl or acyl group having 10–40 carbon atoms, which may be substituted by a hydroxyl group or into which an oxycarbonyl group (—COO— or —OCO—) may be introduced, and (b) a sulfonating agent selected from the group consisting of vinylsulfonic acid, halogenated $C_{1-5}$ alkanesulfonic acids which may be substituted by a hydroxyl group, and salts thereof.

According to the present invention, there is further provided use of the polysaccharide derivative described above for a thickener for cosmetic compositions.

According to the present invention, there is still further provided a process for thickening cosmetic ingredients, which comprises adding the polysaccharide derivative described above to the cosmetic ingredients.

According to the present invention, there is yet still further provided a cosmetic composition comprising the polysaccharide derivative described above.

The polysaccharide derivative according to the present invention permits the provision of an aqueous solution high in transparency, exhibits excellent thickening ability by its addition in a small amount, undergoes little change in viscosity of its solution even either in coexistence with salts or by temperature changes and moreover permits the provision of an emulsion far excellent in stability. Therefore, the polysaccharide derivative according to the present invention can be widely used as a thickener, gelling agent, excipient, emulsion stabilizer, flocculant and/or the like for cosmetics and toiletries.

The above and other objects, features and advantages of the present invention will become apparent from the following description and the appended claims.

DETAILED DESCRIPTION OF THE PREFERRED EMBODIMENTS

Taking cellulose as an example of a polysaccharide, the novel polysaccharide derivative according to the present invention is represented by the following general formula:

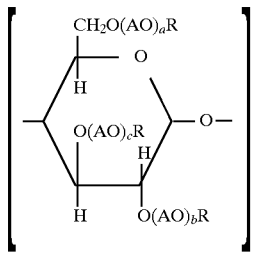

wherein radicals R are the same or different from one another and are individually a radical selected from (1) a hydrogen atom, a methyl, ethyl, hydroxyethyl or hydroxypropyl group, or the like, (2) the hydrophobic substituent (A), or (3) the sulfoalkyl group (B) which may be substituted by a hydroxyl group, radicals A are the same or different from one another and are individually an alkylene group having 2–4 carbon atoms, and a, b and c are the same or different from one another and are individually a number of 0–10, with the proviso that although the individual groups AO and radicals R, and a, b and c may be the same or different from one another either in a repeating unit or between repeating units, average degrees of substitution by the substituents (A) and (B) per constitutional monosaccharide residue are 0.001–1.0 and 0.01–2.0, respectively, and the remainder is the radical (1).

In the polysaccharide derivative according to the present invention, the radicals R in the repeating unit represented by the above general formula include the hydrophobic substituent (A) and the sulfoalkyl group (B) which may be substituted by a hydroxyl group. However, the substituents (A) and (B) may not be necessarily present in one and the same repeating unit. It is only necessary for the substituents (A) and (B) to be introduced as substituents into a molecule on the whole. The average degrees of substitution by the substituents (A) and (B) per repeating unit are 0.001–1.0 and 0.01–2.0, respectively. The remainder of the radicals R is a radical such as a hydrogen atom, or a methyl, ethyl, hydroxyethyl or hydroxypropyl group as described above.

Examples of the hydrophobic substituent (A) include linear or branched alkyl, alkenyl and acyl groups having 10–40 carbon atoms, which may be substituted by a hydroxyl group or into which an oxycarbonyl group (—COO— or —OCO—) may be introduced, alkylglyceryl ether groups each having a linear or branched alkyl group having 10–40 carbon atoms and alkenylglyceryl ether groups each having a linear or branched alkenyl group having 10–40 carbon atoms. Of these, the alkylglyceryl ether groups each having a linear or branched alkyl group having 10–40 carbon atoms and the alkenylglyceryl ether groups each having a linear or branched alkenyl group having 10–40 carbon atoms are preferred.

The linear alkyl groups among the alkyl and alkenyl groups having 10–40 carbon atoms in the hydrophobic substituents (A) include decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hentriacontyl, dotriacontyl, tritriacontyl, tetratriacontyl, pentatriacontyl, hexatriacontyl, heptatriacontyl, octatriacontyl, nonatriacontyl and tetracontyl groups. The branched alkyl groups include methylundecyl, methylheptadecyl, ethylhexadecyl, methyloctadecyl, propylpentadecyl, 2-hexyldecyl, 2-octyldodecyl, 2-heptylundecyl, 2-decyltetradecyl, 2-dodecylhexadecyl, 2-tetradecyloctadecyl and 2-tetradecylbehenyl groups, and the like. The alkenyl groups include decenyl, undecenyl, dodecenyl, tridecenyl, tetradecenyl, pentadecenyl, hexadecenyl, heptadecenyl, octadecenyl, nonadecenyl, eicocenyl, heneicocenyl, dococenyl, tricocenyl, tetracocenyl, pentacocenyl, hexacocenyl, hexacocenyl, heptacocenyl, octacocenyl, nonacocenyl, triacontenyl, oleyl, linoleyl and linolenyl groups, and the like. Of these, the linear or branched alkyl and alkenyl groups having 12–36 carbon atoms, particularly, 16–24 carbon atoms are preferred, with the alkyl groups, particularly, the linear alkyl groups being more preferred from the viewpoint of stability. Besides the above alkyl and alkenyl groups, examples of the hydrophobic substituents (A) include 2-hydroxyalkyl groups, 1-hydroxymethylalkyl groups, 2-hydroxyalkenyl groups, 1-hydroxymethylalkenyl groups and the like, in which a hydroxyl group is substituted in the above alkyl and alkenyl groups; 1-oxoalkyl groups and 1-oxoalkenyl groups, in which an oxo group is substituted at a 1-position in the above alkyl and alkenyl groups, i.e., acyl groups; and groups obtained by introducing an oxycarbonyl group into the above alkyl and alkenyl groups. However, the alkyl, alkenyl and acyl groups which may be substituted by a hydroxyl group are preferred, with the 2-hydroxyalkyl groups being particularly preferred from the viewpoint of stability and preparation.

Among the above hydrophobic substituents (A), the $C_{1-40}$ alkylglyceryl ether groups and the $C_{1-40}$ alkenylglyceryl ether groups include 2-hydroxy-3-alkoxypropyl, 2-alkoxy-1-(hydroxymethyl)ethyl, 2-hydroxy-3-alkenyloxy-propyl and 2-alkenyloxy-1-(hydroxymethyl)ethyl groups. The $C_{1-40}$ alkyl or $C_{1-40}$ alkenyl groups which are substituted in these glyceryl ether groups include the same groups as mentioned above. Of these, the linear or branched alkyl and alkenyl groups having 12–36 carbon atoms, particularly, 16–24 carbon atoms are preferred, with the alkyl groups, particularly, the linear alkyl groups being more preferred from the viewpoint of stability.

These hydrophobic substituents (A) may be substituted for not only hydrogen atoms of hydroxyl groups directly bonded to a polysaccharide molecule, but also hydrogen atoms of hydroxyl groups in hydroxyethyl and/or hydroxypropyl groups bonded to a polysaccharide molecule. The degree of substitution by these hydrophobic substituents (A) may be suitably controlled within a range of 0.001–1.0 per constitutional monosaccharide residue. However, it preferably falls within a range of 0.003–0.5, particularly 0.004–0.1 per constitutional monosaccharide residue.

Examples of the sulfoalkyl group (B) which may be substituted by a hydroxyl group include 2-sulfoethyl, 3-sulfopropyl, 3-sulfo-2-hydroxypropyl and 2-sulfo-1-(hydroxymethyl)ethyl groups, with the 3-sulfo-2-hydroxypropyl group being preferred from the viewpoint of stability and preparation. These substituents (B) may form salts with an alkali metal such as Na or K, an alkaline earth metal such as Ca or Mg, an organic cationic group such as that in an amine, an ammonium ion, or the like at the whole or a part thereof. These substituents (B) may also be substituted for not only hydrogen atoms of hydroxyl groups directly bonded to a polysaccharide molecule, but also hydrogen atoms of hydroxyl groups in hydroxyethyl and/or hydroxypropyl groups bonded to a polysaccharide molecule. The degree of substitution by these substituents (B) may be suitably controlled within a range of 0.01–2.0 per constitutional monosaccharide residue according to the degree of introduction of the hydrophobic substituent (A), and the like. However, it preferably falls within a range of 0.02–1.5, more preferably 0.1–0.7, particularly 0.2–0.5 per constitutional monosaccharide residue.

The polysaccharide derivative according to the present invention can be prepared by reacting a polysaccharide or a derivative thereof, either by stages or at the same time, with (a) a hydrophobizing agent selected from the group consisting of glycidyl ether compounds, epoxides, halides, halohydrins, esters, acid anhydrides and acyl halides each having a hydrophobic group containing a linear or branched alkyl, alkenyl or acyl group having 10–40 carbon atoms, which may be substituted by a hydroxyl group or into which an oxycarbonyl group (—COO— or —OCO—) may be introduced, and (b) a sulfonating agent selected from the group consisting of vinylsulfonic acid, halogenated $C_{1-5}$ alkanesulfonic acids which may be substituted by a hydroxyl group, and salts thereof.

More specifically, the preparation process of the polysaccharide derivative according to the present invention is carried out by partially hydrophobizing hydrogen atoms of hydroxyl groups in a polysaccharide or a derivative thereof [introduction of the hydrophobic substituent (A)], and then sulfonating the whole or a part of hydrogen atoms of the remaining hydroxyl groups [introduction of the substituent (B) having a sulfonic group], or first conducting the sulfonation reaction and then performing the hydrophobization reaction, or conducting the hydrophobization reaction and the sulfonation reaction at the same time.

Examples of the polysaccharide or the derivative thereof useful in the practice of the present invention include cellulose, guar gum, starch, hydroxyethyl cellulose, hydroxyethyl guar gum, hydroxyethyl starch, methyl cellulose, methyl guar gum, methyl starch, ethyl cellulose, ethyl guar gum, ethyl starch, hydroxypropyl cellulose, hydroxypropyl guar gum, hydroxypropyl starch, hydroxyethylmethyl cellulose, hydroxyethylmethyl guar gum, hydroxyethylmethyl starch, hydroxypropylmethyl cellulose, hydroxypropylmethyl guar gum and hydroxypropylmethyl starch. Of these, cellulose, hydroxyethyl cellulose, methyl cellulose, ethyl cellulose, hydroxypropyl cellulose are preferred, with hydroxyethyl cellulose being particularly preferred. The substituents of these polysaccharides, such as methyl, ethyl, hydroxyethyl and hydroxypropyl groups may be introduced either singly or in any combination thereof. A degree of substitution by the substituents is preferably 0.1–10, particularly 0.5–5 per constitutional monosaccharide residue. The polysaccharides or the derivatives thereof preferably have a weight average molecular weight ranging from 10,000 to 10,000,000, more preferably from 100,000 to 5,000,000, particularly preferably from 300,000 to 2,000,000.

The hydrophobization reaction and the sulfonation reaction will hereinafter be described separately. As described above, either the hydrophobization reaction or the sulfonation reaction may be first conducted, or the both reaction may be conducted at the same time. However, it is preferable to conduct the sulfonation reaction after conducting the hydrophobization reaction.

<Hydrophobization reaction>

The hydrophobization reaction of a polysaccharide, a sulfonated polysaccharide or a derivative thereof is conducted by dissolving or dispersing the polysaccharide, the sulfonated polysaccharide or the derivative thereof in a suitable solvent to react with the hydrophobizing agent (a).

Of the hydrophobizing agents (a) described above, the glycidyl ether compounds, epoxides, halides and acyl halides are particularly preferred. These hydrophobizing agents (a) may be used either singly or in any combination thereof. The amount of the hydrophobizing agent (a) to be used may be suitably controlled according to the desired degree of introduction of the hydrophobic substituent into the polysaccharide, the sulfonated polysaccharide or the derivative thereof. However, it is generally preferable to control the amount within a range of 0.001–10 equivalents, particularly 0.003–1 equivalent per constitutional monosaccharide reside of the polysaccharide, the sulfonated polysaccharide or the derivative thereof.

The hydrophobization reaction is preferably carried out in the presence of an alkali as needed. No particular limitation is imposed on such an alkali. Examples thereof include the hydroxides, carbonates and bicarbonates of alkali metals and alkaline earth metals. Of these, sodium hydroxide, potassium hydroxide, calcium hydroxide and magnesium hydroxide are preferred. The amount of the alkali to be used is 0.01–10 moles per mole of the hydrophobizing agent (a) to be used. In particular, 0.1–10 moles are preferred because better results can be given.

Examples of the solvent include lower alcohols, for example, isopropyl alcohol and tert-butyl alcohol. A mixed solvent obtained by adding water in a proportion of 1–50 wt. %, preferably 2–30 wt. % to a lower alcohol may be used with a view toward swelling the polysaccharide, the sulfonated polysaccharide or the derivative thereof to enhance its reactivity to the hydrophobizing agent (a), thereby conducting the reaction.

The reaction is preferably conducted at a temperature within a range of 0°–200° C., particularly 30°–100° C. After completion of the reaction, the alkali is neutralized with an acid. As the acid, there may be used an inorganic acid such as sulfuric acid, hydrochloric acid or phosphoric acid, or an organic acid such as acetic acid. The subsequent reaction may be conducted without neutralizing the alkali after the hydrophobization reaction.

When the hydrophobized polysaccharide thus obtained is then used in the sulfonation reaction, it may be separated by filtration or the like and used as it is. However, it may be washed with a solvent such as hot water, water-containing isopropyl alcohol or water-containing acetone to remove an unreacted hydrophobizing agent (a) and salts secondarily produced by the neutralization and the like, as needed, and then used. Incidentally, when the sulfonation reaction has been already conducted prior to the hydrophobization reaction, the hydrophobized polysaccharide may be separated by filtration or the like, then subjected to washing, neutralization and/or the like as needed, and then dried, thereby obtaining the polysaccharide derivative according to the present invention.

<Sulfonation reaction>

The sulfonation reaction of a polysaccharide, a hydrophobized polysaccharide or a derivative thereof is conducted by dissolving or dispersing the polysaccharide, the hydrophobized polysaccharide or the derivative thereof in a suitable solvent to react with the sulfonating agent (b).

In the sulfonating agents (b), examples of the substituent halogen atom of the halogenated $C_{1-5}$ alkanesulfonic acids which may be substituted by a hydroxyl group include fluorine, chlorine and bromine atoms. Preferred sulfonating agents (b) are vinylsulfonic acid, 3-halo-2-hydroxypropanesulfonic acids and 3-halopropanesulfonic acids. These sulfonating agents (b) may be used either singly or in any combination thereof. The amount of the sulfonating agent (b) to be used may be suitably controlled according to the desired degree of introduction of a sulfonic group into the polysaccharide, the hydrophobized polysaccharide or the derivative thereof. However, it is generally preferable to control the amount within a range of 0.1–10 equivalents, particularly 0.2–5 equivalents per constitutional monosaccharide reside of the polysaccharide, the hydrophobized polysaccharide or the derivative thereof.

The sulfonation reaction is preferably carried out in the presence of an alkali as needed. No particular limitation is imposed on such an alkali. Examples thereof include the hydroxides, carbonates and bicarbonates of alkali metals and alkaline earth metals. Of these, sodium hydroxide, potassium hydroxide, calcium hydroxide and magnesium hydroxide are preferred. The amount of the alkali to be used is 1.0–3.0 moles per mole of the sulfonating agent (b) to be used. In particular, 1.05–1.5 moles are preferred because better results can be given.

Examples of the solvent include lower alcohols, for example, isopropyl alcohol and tert-butyl alcohol. A mixed solvent obtained by adding water in a proportion of 0.1–100 wt. %, preferably 1–50 wt. % to a lower alcohol may be used with a view toward enhancing the reactivity of the polysaccharide, the hydrophobized polysaccharide or the derivative thereof to the sulfonating agent (b), thereby conducting the reaction.

The reaction is preferably conducted at a temperature within a range of 0°–150° C., particularly 30°–100° C. After completion of the reaction, the alkali is neutralized with an acid. As the acid, there may be used an inorganic acid such as sulfuric acid, hydrochloric acid or phosphoric acid, or an organic acid such as acetic acid. The subsequent reaction may be conducted without neutralizing the alkali after the sulfonation reaction.

When the sulfonated polysaccharide thus obtained is then used in the hydrophobization reaction, it may be separated by filtration or the like and used as it is. However, it may be washed with a solvent such as hot water, water-containing isopropyl alcohol or water-containing acetone to remove an unreacted sulfonating agent (b) and salts secondarily produced by the neutralization and the like, as needed, and then used. Incidentally, when the hydrophobization reaction has been already conducted prior to the sulfonation reaction, the sulfonated polysaccharide may be separated by filtration or the like, then subjected to washing, neutralization and/or the like as needed, and then dried, thereby obtaining the polysaccharide derivative according to the present invention.

The polysaccharide derivative according to the present invention permits the provision of an aqueous solution high in transparency, exhibits excellent thickening ability by its addition in a small amount to cosmetic ingredients, undergoes little change in viscosity of its solution even either in coexistence with salts or by temperature changes and moreover permits the provision of an emulsion far excellent in stability. Therefore, the polysaccharide derivative according to the present invention can be widely used as a thickener, gelling agent, excipient, emulsion stabilizer, flocculant and/or the like for cosmetics and toiletries.

When the polysaccharide derivative according to the present invention is used in a cosmetic composition, no particular limitation is imposed on its amount to be incorporated into cosmetic ingredients. However, the amount is preferably 0.01–10 wt. %, particularly 0.05–3 wt. %.

When the polysaccharide derivative according to the present invention is used in a skin cosmetic composition, it may be incorporated in combination with ingredients employed routinely as skin cosmetic ingredients, such as surfactants, oily substances, moisturizers, film-forming agents, oil-gelling agents, metal oxides, organic ultraviolet absorbents, inorganic metal salts, organic metal salts, alcohols, chelating agents, pH adjustors, antiseptics, other thickeners, medicinally-effective ingredients, coloring matter and perfume bases, as needed, thereby providing the cosmetic composition in various forms, for example, oil/water or water/oil type emulsified cosmetics, creams, cosmetic emulsions, toilet waters, oily cosmetics, lipsticks, foundations, skin cleansers, etc.

When the polysaccharide derivative according to the present invention is used in a hair cosmetic composition, it may be incorporated in combination with ingredients employed routinely as hair cosmetic ingredients, such as surfactants, other thickeners, oil-gelling agents, metal oxides, organic ultraviolet absorbents, inorganic metal salts, organic metal salts, pearl-like-hue-imparting agents, antioxidants, antiseptics, medicinally-effective ingredients, coloring matter and perfume bases, as needed. In order to improve a feel of hair to the touch, it may be incorporated together with cationic polymers such as cationized cellulose, and/or silicone derivatives such as dimethylpolysiloxane, amino-modified silicone and polyether-modified silicone. No particular limitation is imposed on the form of the hair cosmetic composition, and it may be provided as common hair cosmetic compositions of various forms such as emulsions, suspensions, gel, transparent solutions and aerosol, namely, pre-shampooing agents, shampoos, hair rinses, hair treatments, hair conditioners, blow-conditioning agents and the like.

The cosmetic compositions comprising the polysaccharide derivative according to the present invention give users a pleasant feeling upon use and exhibit excellent viscosity stability. When a metal oxide, an inorganic metal salt, an organic metal salt and/or the like are used in combination, the resultant cosmetic composition can give users a more pleasant feeling upon use and exhibit far excellent viscosity stability. Besides, an organic ultraviolet absorbent is incorporated, whereby the cosmetic composition can be provided as a sunscreen skin-care cosmetic composition which gives users a pleasant feeling upon use and has excellent viscosity stability. Further, when a metal oxide and an organic ultraviolet absorbent are used in combination, an ultraviolet protective effect can be more enhanced.

Examples of the metal oxide include titanium oxide, zinc oxide, iron oxide, zirconium oxide and cerium oxide. These metal oxides may be subjected to a treatment with silica, silica-alumina, a metallic soap, a fatty acid, an amino acid, silicone, alkylphosphoric acid, fluorine or the like. The metal oxide may be a complex of two or more of these metal oxides or of each of these metal oxides with another organic or inorganic powder. No particular limitation is imposed on the size, shape and the like of these metal oxides. These metal oxides may be incorporated either singly or in any combination thereof. The amount of these metal oxides to be incorporated is preferably 0.001–50 wt. %, particularly 0.005–30 wt. %.

Examples of oil-soluble ultraviolet absorbents among the organic ultraviolet absorbents include benzoic acid type absorbents such as para-aminobenzoic acid (hereinafter abbreviated as "PABA"), glyceryl PABA, ethyldihydroxypropyl PABA, N-ethoxylate PABA ethyl ester, N-dimethyl PABA ethyl ester, N-dimethyl PABA butyl ester, N-dimethyl PABA amyl ester and octyldimethyl PABA; anthranilic acid type absorbents such as homomenthyl-N-acetyl anthranilate; salicylic acid type absorbents such as amyl salicylate, menthyl salicylate, homomenthyl salicylate, octyl salicylate, phenyl salicylate, benzyl salicylate and p-isopropanolphenyl salicylate; cinnamic acid type absorbents such as octyl cinnamate, ethyl-4-isopropyl cinnamate, ethyl-2,4-diisopropyl cinnamate, methyl-2,4-diisopropyl cinnamate, propyl p-methoxycinnamate, isopropyl p-methoxycinnamate, isoamyl p-methoxycinnamate, 2-ethylhexyl p-methoxycinnamate, 2-ethoxyethyl p-methoxycinnamate, cyclohexyl p-methoxycinnamate, ethyl-α-cyano-β-phenyl cinnamate, 2-ethylhexyl-α-cyano-β-phenyl cinnamate and glyceryl mono-2-ethylhexanoyl di-para-methoxycinnamate; benzophenone type absorbents such as 2,4-dihydroxybenzophenone, 2,2'-dihydroxy-4-methoxy-benzophenone, 2,2'-dihydroxy-4,4'-dimethoxybenzophenone, 2-hydroxy-4-methoxybenzophenone, 2-hydroxy-4-methoxy-4'-methylbenzophenone, 4-phenylbenzophenone, 2-ethylhexyl-4'-phenylbenzophenone-2-carboxylate, 2-hydroxy-4-n-octoxybenzophenone and 4-hydroxy-3-carboxybenzophenone; and besides 3-(4'-methylbenzylidene)-dl-camphor, 3-benzylidene-dl-camphor, ethyl urocanate, 2-phenyl-3-methylbenzoxazole, 2,2'-hydroxy-5-methylphenylbenzotriazole, 2-(2'-hydroxy-5-tert-octylphenyl)benzotriazole, dibenzalazine, dianisoylmethane, 4-methoxy-4'-tert-butyl-benzoylmethane, 5-(3,3-dimethyl-2-norbornylidene)-3-pentan-2-one, benzene bis-1,3-diketone derivatives described in Japanese Patent Application Laid-Open No. 212579/1990 and benzoylpinacolone derivatives described in Japanese Patent Application Laid-Open No. 220153/1991.

Examples of water-soluble ultraviolet absorbents include diethanolamine p-methoxycinnanate, sodium 2-hydroxy-4-methoxybenzophenone-5-sulfonate, tetrahydroxybenzophenone, methyl hesperidin, sodium 3-hydroxy-4-methoxycinnamate, sodium ferulate, urocanic acid, and extracts of animals and plants such as milfoil, aloe, marsh mallow, burdock and sage, which have an ultraviolet-absorbing effect.

These ultraviolet absorbents may be incorporated either singly or in any combination thereof. The amount of the absorbents to be incorporated is preferably 0.001–50 wt. %, particularly 0.005–30 wt. %.

The inorganic metal salts and organic metal salts include all of monovalent metal salts, divalent metal salts and trivalent metal salts used in cosmetic compositions. Specific examples thereof include sodium sulfate, potassium sulfate, magnesium sulfate, magnesium chloride, sodium chloride, zinc chloride, zinc sulfate, aluminum potassium sulfate, aluminum chloride, ferric chloride, zinc p-phenolsulfonate, and monovalent metal salts, divalent metal salts and trivalent metal salts of organic acids such as lactic acid, tartaric acid, succinic acid and citric acid. These metal salts may be used either singly or in any combination thereof. The amount of the metal salts to be incorporated is preferably 0.001–30 wt. %, particularly 0.005–20 wt. %.

The other thickeners include polysaccharides such as xanthan gum, hyaluronic acid and acid heteropolysaccharide derived from callus of a plant belonging to *Polyanthes L.*, and derivatives thereof. The film-forming agents include polyvinyl alcohol, soluble collagen, polyethylene glycol having a molecular weight of 20,000–4,000,000, and the like. The oil-gelling agents include dextrin fatty acid esters and the like.

The medicinally-effective ingredients include extracts of plants such as hamamelis, peony, chamomile and chamomilla; amino acids such as glycine and serine, and derivatives thereof; oligopeptides; guanidine derivatives described in Japanese Patent Application Laid-Open No. 228023/1994; antiphlogistics such as glycyrrhizin and salts thereof, glycyrrhetin and salts thereof, allantoin, epsilon-aminocapronic acid and salts thereof; vitamins such as α-carotene, β-carotene, ascrobic acid and tocopherol; antioxidants such as tannins and flavonoid; hydroxy acids such as 6-hydroxyhexanoic acid, 8-hydroxyundecanoic acid, 9-hydroxyundecanoic acid, 10-hydroxyundecanoic acid and 11-hydroxyundecanoic acid, and salts thereof; amine derivatives such as 1-(2-hydroxyethylamino)-3-isostearyloxy-2-propanol, 1-(2-hydroxyethylamino)-3-(12-hydroxystearyloxy)-2-propanol and 1-(2-hydroxyethylamino)-3-methyloxy-2-propanol; and the like.

The present invention will hereinafter be described in more detail by the following Examples. However, the present invention is not limited to these examples.

In the following Examples, the degrees of substitution by a hydrophobic substituent in novel polysaccharide derivatives according to the present invention were determined by NMR making use of deutero-DMSO as a solvent, while the degrees of substitution by a sulfonic group were determined by elemental analysis (S atom) and colloidal titration. More specifically, a solution containing a thickener at an already-known concentration was prepared in advance. Added to this solution were an already-known weight of a 1/200N solution of methyl glycol chitosan and further several drops of a solution of a toluidine blue indicator. The resultant mixture was subjected to back titration with a 1/400N solution of potassium polyvinylsulfate to determine the amount of the sulfonic group from the titre.

In the following Examples, the term "degree of substitution" means the number of substituents per constitutional monosaccharide residue.

EXAMPLE 1

(1) A 1,000-ml glass separable reactor equipped with a stirrer, thermometer and condenser tube was charged with 50 g of hydroxyethyl cellulose (HEC-QP4400, product of Union Carbide Corp.) having a weight average molecular weight of about 800,000 and a degree of substitution by a hydroxyethyl group of 1.8, 400 g of 88% isopropyl alcohol and 3.5 g of a 48% aqueous solution of sodium hydroxide to prepare a slurry. The slurry was stirred at room temperature for 30 minutes in a nitrogen atmosphere. To the slurry, 5.4 g of stearylglycidyl ether were added to conduct a reaction at 80° C. for 8 hours, thereby performing hydrophobization. After completion of the hydrophobization reaction, the liquid reaction mixture was neutralized with acetic acid, and the resultant reaction product was collected by filtration. The reaction product was washed twice with 500 g of 80% acetone and then twice with 500 g of acetone, and dried at 70° C. for 24 hours under reduced pressure, thereby obtaining 49.4 g of a hydrophobized hydroxyethyl cellulose derivative.

(2) A 500-ml glass separable reactor equipped with a stirrer, thermometer and condenser tube was charged with 10.0 g of the hydrophobized hydroxyethyl cellulose derivative obtained in the step (1), 80.0 g of isopropyl alcohol and 0.33 g of a 48% aqueous solution of sodium hydroxide to prepare a slurry. The slurry was stirred at room temperature for 30 minutes in a nitrogen atmosphere. A mixture composed of 6.4 g of sodium 3-chloro-2-hydroxypropanesulfonate, 2.7 g of a 48% aqueous solution of sodium hydroxide and 20.0 g of water was added to the resultant liquid reaction mixture to conduct sulfonation at 50° C. for 9 hours. After completion of the reaction, the liquid reaction mixture was neutralized with acetic acid, and the resultant reaction product was collected by filtration. The reaction product was washed 3 times with 500 g of 80% acetone (containing 20% of water) and then twice with 500 g of acetone, and then dried at 70° C. for 24 hours under reduced pressure, thereby obtaining 7.2 g of a hydroxyethyl cellulose derivative (Invention Product 1) substituted by a stearylglyceryl ether group and a sulfo-2-hydroxypropyl group.

The degrees of substitution by the stearylglyceryl ether group and the sulfo-2-hydroxypropyl group in the thus-obtained hydroxyethyl cellulose derivative were 0.030 and 0.15, respectively.

EXAMPLE 2

After hydrophobization was conducted in the same manner as in Example 1 except that the amount of stearylglycidyl ether was changed to 10.8 g, sulfonation was performed in the same manner as in Example 1 except that the amounts of 3-chloro-2-hydroxy-propanesulfonate and the 48% aqueous solution of sodium hydroxide were changed to 9.6 g and 4.0 g from 2.7 g, respectively, thereby obtaining a hydroxyethyl cellulose derivative (Invention Product 2).

The degrees of substitution by the stearylglyceryl ether group and the sulfo-2-hydroxypropyl group in the thus-obtained hydroxyethyl cellulose derivative were 0.058 and 0.20, respectively.

EXAMPLE 3

A 500-ml glass separable reactor equipped with a stirrer, thermometer and condenser tube was charged with 10.0 g of the hydrophobized hydroxyethyl cellulose obtained in the step (1) of Example 1, 160 g of isopropyl alcohol and 18 g of a 25% aqueous solution of sodium vinylsulfonate to prepare a slurry. After the slurry was stirred at room temperature for 30 minutes in a nitrogen atmosphere, 1.2 g of a 48% aqueous solution of sodium hydroxide were charged, and the resultant slurry mixture was further stirred at room temperature for 60 minutes in a nitrogen atmosphere. The slurry was heated up to 80° C and stirred at 80° C. for 2 hours to conduct sulfonation. After completion of the reaction, the liquid reaction mixture was cooled down to 60° C. and neutralized with acetic acid, and the resultant reaction product was collected by filtration. The reaction product was washed 3 times with 500 g of 80% acetone (containing 20% of water) and then twice with 500 g of acetone, and then dried at 700C for 24 hours under reduced pressure, thereby obtaining 8.9 g of a hydroxyethyl cellulose derivative (Invention Product 3) substituted by a stearylglyceryl ether group and a sulfoethyl group.

The degrees of substitution by the stearylglyceryl ether group and the sulfoethyl group in the thus-obtained hydroxyethyl cellulose derivative were 0.030 and 0.18, respectively.

EXAMPLE 4

The same hydrophobized hydroxyethyl cellulose as that used in Example 2 was sulfonated in the same manner as in Example 3 except that the amount of the 25% aqueous solution of sodium vinylsulfonate was changed to 36.0 g, thereby obtaining a hydroxyethyl cellulose derivative (Invention Product 4) substituted by a stearylglyceryl ether group and a sulfoethyl group.

The degrees of substitution by the stearylglyceryl ether group and the sulfoethyl group in the thus-obtained hydroxyethyl cellulose derivative were 0.058 and 0.34, respectively.

EXAMPLE 5

A 500-ml glass separable reactor equipped with a stirrer, thermometer and condenser tube was charged with 10.0 g of the hydrophobized hydroxyethyl cellulose obtained in the step (1) of Example 1, 160 g of 90% isopropyl alcohol and 7.2 g of a 48% aqueous solution of sodium hydroxide to prepare a slurry. The slurry was stirred at room temperature for 30 minutes in a nitrogen atmosphere. After the liquid reaction mixture was cooled down to 10° C. or lower with ice water, 15.0 g of sodium 3-bromopropanesulfonate were charged, and the resultant mixture was stirred for 60 minutes at 10° C. or lower. The liquid reaction mixture was heated up to 80° C. and stirred at 80° C. for 2 hours to conduct sulfonation. After completion of the reaction, the liquid reaction mixture was cooled down to 60° C. and neutralized with acetic acid, and the resultant reaction product was collected by filtration. The reaction product was washed 3 times with 500 g of 80% acetone (containing 20% of water) and then twice with 500 g of acetone, and then dried at 70° C. for 24 hours under reduced pressure, thereby obtaining 8.9 g of a hydroxyethyl cellulose derivative (Invention Product 5) substituted by a stearylglyceryl ether group and a sulfopropyl group.

The degrees of substitution by the stearylglyceryl ether group and the sulfopropyl group in the thus-obtained hydroxyethyl cellulose derivative were 0.030 and 0.10, respectively.

EXAMPLE 6

(1) A 1,000-ml glass separable reactor equipped with a stirrer, thermometer and condenser tube was charged with 50 g of hydroxyethyl cellulose (HEC-QP4400, product of Union Carbide Corp.) having a weight average molecular weight of about 800,000 and a degree of substitution by a hydroxyethyl group of 1.8, 400 g of 88% isopropyl alcohol and 3.5 g of a 48% aqueous solution of sodium hydroxide to prepare a slurry. The slurry was stirred at room temperature for 30 minutes in a nitrogen atmosphere. To the slurry, 8.5 g of palmitylglycidyl ether were added to conduct a reaction at 80° C. for 9 hours, thereby performing hydrophobization. After completion of the hydrophobization reaction, the liquid reaction mixture was neutralized with acetic acid, and the resultant reaction product was collected by filtration. The reaction product was washed twice with 500 g of 80% acetone and then twice with 500 g of acetone, and dried at 70° C. for 24 hours under reduced pressure, thereby obtaining 50.3 g of a hydrophobized hydroxyethyl cellulose derivative.

(2) A 500-ml glass separable reactor equipped with a stirrer, thermometer and condenser tube was charged with 10.0 g of the hydrophobized hydroxyethyl cellulose obtained in the step (1), 160 g of isopropyl alcohol and 36.0 g of a 25% aqueous solution of sodium vinylsulfonate to prepare a slurry. After the slurry was stirred at room temperature for 30 minutes in a nitrogen atmosphere, 1.2 g of a 48% aqueous solution of sodium hydroxide were charged, and the resultant slurry mixture was further stirred at room temperature for 60 minutes in a nitrogen atmosphere. The slurry was heated up to 80° C. and stirred at 80° C. for 2 hours to conduct sulfonation. After completion of the reaction, the liquid reaction mixture was cooled down to 60° C. and neutralized with acetic acid, and the resultant reaction product was collected by filtration. The reaction product was washed 3 times with 500 g of 80% acetone (containing 20% of water) and then twice with 500 g of acetone, and then dried at 70° C. for 24 hours under reduced pressure, thereby obtaining 8.9 g of a hydroxyethyl cellulose derivative (Invention Product 6) substituted by a palmitylglyceryl ether group and a sulfoethyl group.

The degrees of substitution by the palmitylglyceryl ether group and the sulfoethyl group in the thus-obtained hydroxyethyl cellulose derivative were 0.060 and 0.35, respectively.

EXAMPLE 7

(1) A 1,000-ml glass separable reactor equipped with a stirrer, thermometer and condenser tube was charged with 50 g of methyl cellulose (Metholose SM-800, product of Shin-Etsu Chemical Co., Ltd.) having a weight average molecular weight of about 400,000 and a degree of substitution by a methyl group of 1.8, 400 g of isopropyl alcohol and 4.5 g of a 48% aqueous solution of sodium hydroxide. The contents were stirred at room temperature for 30 minutes in a nitrogen atmosphere. To the resultant mixture, 6.0 g of stearylglycidyl ether were added to conduct a reaction at 80° C. for 8 hours, thereby performing hydrophobization. After completion of the hydrophobization reaction, the liquid reaction mixture was neutralized with acetic acid, and the resultant reaction product was collected by filtration. The reaction product was washed twice with 500 g of 80% acetone and then twice with 500 g of acetone, and dried at 70° C. for 24 hours under reduced pressure, thereby obtaining 48.5 g of hydrophobized methyl cellulose.

(2) A 500-ml glass separable reactor equipped with a stirrer, thermometer and condenser tube was charged with 10.0 g of the hydrophobized methyl cellulose obtained in the step (1), 80.0 g of isopropyl alcohol and 0.33 g of a 48% aqueous solution of sodium hydroxide to prepare a slurry. The slurry was stirred at room temperature for 30 minutes in a nitrogen atmosphere. A mixture composed of 7.7 g of sodium 3-chloro-2-hydroxypropanesulfonate, 3.2 g of a 48% aqueous solution of sodium hydroxide and 20.0 g of water was added to the resultant liquid reaction mixture to conduct sulfonation at 50° C. for 8 hours. After completion of the reaction, the liquid reaction mixture was neutralized with acetic acid, and the resultant reaction product was collected by filtration. The reaction product was washed 3 times with 500 g of 80% acetone (containing 20% of water) and then twice with 500 g of acetone, and then dried at 70° C. for 24 hours under reduced pressure, thereby obtaining 8.3 g of a methyl cellulose derivative (Invention Product 7) substituted by a stearylglyceryl ether group and a sulfo-2-hydroxypropyl group.

The degrees of substitution by the stearylglyceryl ether group and the sulfo-2-hydroxypropyl group in the thus-obtained methyl cellulose derivative were 0.027 and 0.15, respectively.

EXAMPLE 8

A 500-ml glass separable reactor equipped with a stirrer, thermometer and condenser tube was charged with 10.0 g of the hydrophobized methyl cellulose obtained in the step (1) of Example 7, 160 g of isopropyl alcohol and 21.6 g of a 25% aqueous solution of sodium vinylsulfonate to prepare a slurry. After the slurry was stirred at room temperature for 30 minutes in a nitrogen atmosphere, 1.5 g of a 48% aqueous solution of sodium hydroxide were charged, and the resultant slurry mixture was further stirred at room temperature for 60 minutes in a nitrogen atmosphere. The slurry was heated up to 80° C. and stirred at 80° C. for 2 hours to conduct sulfonation. After completion of the reaction, the liquid reaction mixture was cooled down to 60° C. and neutralized with acetic acid, and the resultant reaction product was collected by filtration. The reaction product was washed 3 times with 500 g of 80% acetone (containing 20% of water) and then twice with 500 g of acetone, and then dried at 70° C. for 24 hours under reduced pressure, thereby obtaining 8.9 g of a methyl cellulose derivative (Invention Product 8) substituted by a stearylglyceryl ether group and a sulfoethyl group.

The degrees of substitution by the stearylglyceryl ether group and the sulfoethyl group in the thus-obtained methyl cellulose derivative were 0.027 and 0.17, respectively.

EXAMPLE 9

A 500-ml glass separable reactor equipped with a stirrer, thermometer and condenser tube was charged with 16.2 g of cellulose powder (product of Merck & Co.), 250 g of tert-butyl alcohol and 52.0 g of a 25% aqueous solution of sodium vinylsulfonate to prepare a slurry. The slurry was stirred at room temperature for 30 minutes in a nitrogen atmosphere. Further, 8.0 g of sodium hydroxide powder were added, and the slurry mixture was stirred at room temperature for 60 minutes in a nitrogen atmosphere. The reaction temperature was raised to 80° C., and the slurry mixture was stirred at 80° C. for 2 hours to conduct sulfonation. After the liquid reaction mixture was cooled down to 60° C., 21.0 g of water were added, and 3.2 g of stearylglycidyl ether were further added. The resultant mixture was heated up to 80° C. and stirred at 80° C. for 8 hours to conduct hydrophobization. After completion of the reaction, the liquid reaction mixture was cooled down to 60° C., and acetic acid was added to neutralize an excess amount of the alkali. Thereafter, the liquid reaction mixture was filtered to obtain cake.

The cake thus obtained was washed 5 times with 500 g of 80% acetone (containing 20% of water) and then twice with 500 g of acetone, and then dried at 70° C. for 24 hours under reduced pressure, thereby obtaining 10.3 g of a cellulose derivative (Invention Product 9) substituted by a stearylglyceryl ether group and a sulfoethyl group.

The degrees of substitution by the stearylglyceryl ether group and the sulfoethyl group in the thus-obtained cellulose derivative were 0.025 and 0.53, respectively.

EXAMPLE 10

Reactions were conducted in the same manner as in Example 9 except that the amount of stearylglycidyl ether was changed to 6.4 g, thereby obtaining a cellulose derivative (Invention Product 10) substituted by a stearylglyceryl ether group and a sulfoethyl group.

The degrees of substitution by the stearylglyceryl ether group and the sulfoethyl group in the thus-obtained cellulose derivative were 0.049 and 0.53, respectively.

EXAMPLE 11

(1) A 1,000-ml glass separable reactor equipped with a stirrer, thermometer and condenser tube was charged with 50 g of hydroxyethyl cellulose (HEC-QP100M, product of Union Carbide Corp.) having a weight average molecular weight of about 1,500,000 and a degree of substitution by a hydroxyethyl group of 1.8, 400 g of 88% isopropyl alcohol and 3 g of a 48% aqueous solution of sodium hydroxide to prepare a slurry. The slurry was stirred at room temperature for 30 minutes in a nitrogen atmosphere. To the slurry, 1.5 g of octadecylglycidyl ether were added to conduct a reaction at 80° C. for 7 hours, thereby performing hydrophobization. After completion of the hydrophobization reaction, the liquid reaction mixture was neutralized with hydrochloric acid, and the resultant reaction product was collected by filtration. The reaction product was washed twice with 500 g of 80% acetone and then twice with 500 g of acetone, and dried at 70° C. for 24 hours under reduced pressure, thereby obtaining 44.3 g of a hydrophobized hydroxyethyl cellulose derivative.

(2) A 500-ml glass separable reactor equipped with a stirrer, thermometer and condenser tube was charged with 10.0 g of the hydrophobized hydroxyethyl cellulose derivative obtained in the step (1), 80.0 g of isopropyl alcohol and 0.33 g of a 48% aqueous solution of sodium hydroxide to prepare a slurry. The slurry was stirred at room temperature for 30 minutes in a nitrogen atmosphere. A mixture composed of 12.8 g of sodium 3-chloro-2-hydroxypropanesulfonate, 5.4 g of a 48% aqueous solution of sodium hydroxide and 20.0 g of water was added to the resultant liquid reaction mixture to conduct sulfonation at 50° C. for 8 hours. After completion of the reaction, the liquid reaction mixture was neutralized with hydrochloric acid, and the resultant reaction product was collected by filtration. The reaction product was washed 3 times with 500 g of 80% acetone (containing 20% of water) and then twice with 500 g of acetone, and then dried at 70° C. for 24 hours under reduced pressure, thereby obtaining 7.5 g of a hydroxyethyl cellulose derivative (Invention Product 11) substituted by an octadecylglyceryl ether group and a 3-sulfo-2-hydroxypropyl group.

The degrees of substitution by the octadecylglyceryl ether group and the 3-sulfo-2-hydroxypropyl group in the thus-obtained hydroxyethyl cellulose derivative were 0.007 and 0.31, respectively.

EXAMPLE 12

(1) A 1,000-ml glass separable reactor equipped with a stirrer, thermometer and condenser tube was charged with 50 g of hydroxyethyl cellulose (HEC-QP100M, product of Union Carbide Corp.) having a weight average molecular weight of about 1,500,000 and a degree of substitution by a hydroxyethyl group of 1.8, 400 g of 88% isopropyl alcohol and 3 g of a 48% aqueous solution of sodium hydroxide to prepare a slurry. The slurry was stirred at room temperature for 30 minutes in a nitrogen atmosphere. To the slurry, 1.0 g of octadecylglycidyl ether was added to conduct a reaction at 80° C. for 7 hours, thereby performing hydrophobization. After completion of the hydrophobization reaction, the liquid reaction mixture was neutralized with hydrochloric acid, and the resultant reaction product was collected by filtration. The reaction product was washed twice with 500 g of 80% acetone and then twice with 500 g of acetone, and dried at 70° C. for 24 hours under reduced pressure, thereby obtaining 45.1 g of a hydrophobized hydroxyethyl cellulose derivative.

(2) A 500-ml glass separable reactor equipped with a stirrer, thermometer and condenser tube was charged with 10.0 g of the hydrophobized hydroxyethyl cellulose derivative obtained in the step (1), 80.0 g of isopropyl alcohol and 0.33 g of a 48% aqueous solution of sodium hydroxide to prepare a slurry. The slurry was stirred at room temperature for 30 minutes in a nitrogen atmosphere. A mixture composed of 12.8 g of sodium 3-chloro-2-hydroxypropanesulfonate, 5.4 g of a 48% aqueous solution of sodium hydroxide and 20.0 g of water was added to the resultant liquid reaction mixture to conduct sulfonation at 50° C. for 8 hours. After completion of the reaction, the liquid reaction mixture was neutralized with hydrochloric acid, and the resultant reaction product was collected by filtration. The reaction product was washed 3 times with 500 g of 80% acetone (containing 20% of water) and then twice with 500 g of acetone, and then dried at 70° C. for 24 hours under reduced pressure, thereby obtaining 7.5 g of a hydroxyethyl cellulose derivative (Invention Product 12) substituted by an octadecylglyceryl ether group and a 3-sulfo-2-hydroxypropyl group.

The degrees of substitution by the octadecylglyceryl ether group and the 3-sulfo-2-hydroxypropyl group in the thus-obtained hydroxyethyl cellulose derivative were 0.004 and 0.31, respectively.

EXAMPLE 13

(1) A 1,000-ml glass separable reactor equipped with a stirrer, thermometer and condenser tube was charged with 50 g of hydroxyethyl cellulose (HEC-QP100M, product of Union Carbide Corp.) having a weight average molecular weight of about 1,500,000 and a degree of substitution by a hydroxyethyl group of 1.8, 400 g of 88% isopropyl alcohol and 3.5 g of a 48% aqueous solution of sodium hydroxide to prepare a slurry. The slurry was stirred at room temperature for 30 minutes in a nitrogen atmosphere. To the slurry, 2.2 g of 1,2-epoxyoctadecane were added to conduct a reaction at 80° C. for 8 hours, thereby performing hydrophobization. After completion of the hydrophobization reaction, the liquid reaction mixture was neutralized with acetic acid, and the resultant reaction product was collected by filtration. The reaction product was washed twice with 500 g of 80% acetone and then twice with 500 g of acetone, and dried at 70° C. for 24 hours under reduced pressure, thereby obtaining 49.4 g of a hydrophobized hydroxyethyl cellulose derivative.

(2) A 500-ml glass separable reactor equipped with a stirrer, thermometer and condenser tube was charged with 10.0 g of the hydrophobized hydroxyethyl cellulose derivative obtained in the step (1), 80.0 g of isopropyl alcohol and 0.33 g of a 48% aqueous solution of sodium hydroxide to prepare a slurry. The slurry was stirred at room temperature for 30 minutes in a nitrogen atmosphere. A mixture composed of 12.8 g of sodium 3-chloro-2-hydroxypropanesulfonate, 5.4 g of a 48% aqueous solution of sodium hydroxide and 20.0 g of water was added to the resultant liquid reaction mixture to conduct sulfonation at 50° C. for 9 hours. After completion of the reaction, the liquid reaction mixture was neutralized with acetic acid, and the resultant reaction product was collected by filtration. The reaction product was washed 3 times with 500 g of 80% acetone (containing 20% of water) and then twice with 500 g of acetone, and then dried at 70° C. for 24 hours under reduced pressure, thereby obtaining 7.2 g of a hydroxyethyl cellulose derivative (Invention Product 13) substituted by a 2-hydroxyoctadecyl group and a 3-sulfo-2-hydroxypropyl group.

The degrees of substitution by the 2-hydroxyoctadecyl group and the 3-sulfo-2-hydroxypropyl group in the thus-obtained hydroxyethyl cellulose derivative were 0.015 and 0.30, respectively.

EXAMPLE 14

A 500-ml glass separable reactor equipped with a stirrer, thermometer and condenser tube was charged with 10.0 g of the hydrophobized hydroxyethyl cellulose obtained in the step (1) of Example 13, 160 g of isopropyl alcohol and 36.0 g of a 25% aqueous solution of sodium vinylsulfonate to prepare a slurry. After the slurry was stirred at room temperature for 30 minutes in a nitrogen atmosphere, 1.2 g of a 48% aqueous solution of sodium hydroxide were charged, and the resultant slurry mixture was further stirred at room temperature for 60 minutes in a nitrogen atmosphere. The slurry was heated up to 80° C. and stirred at 80° C. for 2 hours to conduct sulfonation. After completion of the reaction, the liquid reaction mixture was cooled down to 60° C. and neutralized with acetic acid, and the resultant reaction product was collected by filtration. The reaction product was washed 3 times with 500 g of 80% acetone (containing 20% of water) and then twice with 500 g of acetone, and then dried at 70° C. for 24 hours under reduced pressure, thereby obtaining 8.9 g of a hydroxyethyl cellulose derivative (Invention Product 14) substituted by a 2-hydroxyoctadecyl group and a 2-sulfoethyl group.

The degrees of substitution by the 2-hydroxyoctadecyl group and the 2-sulfoethyl group in the thus-obtained hydroxyethyl cellulose derivative were 0.015 and 0.32, respectively.

EXAMPLE 15

A 500-ml glass separable reactor equipped with a stirrer, thermometer and condenser tube was charged with 10.0 g of the hydrophobized hydroxyethyl cellulose obtained in the step (1) of Example 13, 160 g of 90% isopropyl alcohol and 13.1 g of a 48% aqueous solution of sodium hydroxide to prepare a slurry. The slurry was stirred at room temperature for 30 minutes in a nitrogen atmosphere. After the liquid reaction mixture was cooled down to 10° C. or lower with ice water, 30.0 g of sodium 3-bromopropanesulfonate were charged, and the resultant mixture was stirred for 60 minutes at 10° C. or lower. The liquid reaction mixture was heated up to 80° C. and stirred at 80° C. for 2 hours to conduct sulfonation. After completion of the reaction, the liquid reaction mixture was cooled down to 60° C. and neutralized with acetic acid, and the resultant reaction product was collected by filtration. The reaction product was washed 3 times with 500 g of 80% acetone (containing 20% of water) and then twice with 500 g of acetone, and then dried at 70° C. for 24 hours under reduced pressure, thereby obtaining 8.9 g of a hydroxyethyl cellulose derivative (Invention Product 15) substituted by a 2-hydroxyoctadecyl group and a 3-sulfopropyl group.

The degrees of substitution by the 2-hydroxyoctadecyl group and the sulfopropyl group in the thus-obtained hydroxyethyl cellulose derivative were 0.015 and 0.20, respectively.

EXAMPLE 16

(1) A 1,000-ml glass separable reactor equipped with a stirrer, thermometer and condenser tube was charged with 50 g of hydroxyethyl cellulose (HEC-QP100M, product of Union Carbide Corp.) having a weight average molecular weight of about 1,500,000 and a degree of substitution by a hydroxyethyl group of 1.8, 400 g of 88% isopropyl alcohol and 4.7 g of a 48% aqueous solution of sodium hydroxide to prepare a slurry. The slurry was stirred at room temperature for 30 minutes in a nitrogen atmosphere. To the slurry, 4.8 g of l-chlorooctadecane were added to conduct a reaction at 80° C. for 8 hours, thereby performing hydrophobization. After completion of the hydrophobization reaction, the liquid reaction mixture was neutralized with acetic acid, and the resultant reaction product was collected by filtration. The reaction product was washed twice with 500 g of 80% acetone and then twice with 500 g of acetone, and dried at 70° C. for 24 hours under reduced pressure, thereby obtaining 48.7 g of a hydrophobized hydroxyethyl cellulose derivative.

(2) A 500-ml glass separable reactor equipped with a stirrer, thermometer and condenser tube was charged with 10.0 g of the hydrophobized hydroxyethyl cellulose derivative obtained in the step (1), 80.0 g of isopropyl alcohol and 0.33 g of a 48% aqueous solution of sodium hydroxide to prepare a slurry. The slurry was stirred at room temperature for 30 minutes in a nitrogen atmosphere. A mixture composed of 12.8 g of sodium 3-chloro-2-hydroxypropanesulfonate, 5.4 g of a 48% aqueous solution of sodium hydroxide and 20.0 g of water was added to the resultant liquid reaction mixture to conduct sulfonation at 50° C. for 9 hours. After completion of the reaction, the liquid reaction mixture was neutralized with acetic acid, and the resultant reaction product was collected by filtration. The reaction product was washed 3 times with 500 g of 80% acetone (containing 20% of water) and then twice with 500 g of acetone, and then dried at 70° C. for 24 hours under reduced pressure, thereby obtaining 8.2 g of a hydroxyethyl cellulose derivative (Invention Product 16) substituted by an octadecyl group and a 3-sulfo-2-hydroxypropyl group.

The degrees of substitution by the octadecyl group and the 3-sulfo-2-hydroxypropyl group in the thus-obtained hydroxyethyl cellulose derivative were 0.010 and 0.31, respectively.

EXAMPLE 17

(1) A glass separable reactor equipped with a stirrer, thermometer and condenser tube was charged with 50 g of hydroxyethyl cellulose (HEC-QP100M, product of Union Carbide Corp.) having a weight average molecular weight of about 1,500,000 and a degree of substitution by a hydroxyethyl group of 1.8, 800 g of isopropyl alcohol and 3.5 g of a 48% aqueous solution of sodium hydroxide to prepare a slurry. The slurry was stirred at room temperature for 30 minutes in a nitrogen atmosphere. A mixture composed of 32.8 g of sodium 3-chloro-2-hydroxypropanesulfonate, 17.3 g of a 48% aqueous solution of sodium hydroxide and 200 g of water was added to the resultant liquid reaction mixture to conduct sulfonation at 50° C. for 9 hours. After completion of the reaction, the liquid reaction mixture was neutralized with acetic acid, and the resultant reaction product was collected by filtration. The reaction product was washed twice with 500 g of 80% acetone (containing 20% of water) and then twice with 500 g of acetone, and then dried at 70° C. for 24 hours under reduced pressure, thereby obtaining 52 g of a sulfonated hydroxyethyl cellulose derivative.

(2) A 1,000-ml glass separable reactor equipped with a stirrer, thermometer and condenser tube was charged with 10.0 g of the sulfonated hydroxyethyl cellulose derivative obtained in the step (1), 80.0 g of 88% isopropyl alcohol and 0.73 g of a 48% aqueous solution of sodium hydroxide to prepare a slurry. The slurry was stirred at room temperature for 30 minutes in a nitrogen atmosphere. To the slurry, 0.44 g of stearoyl chloride were added to conduct a reaction at 80° C. for 8 hours, thereby performing hydrophobization. After completion of the hydrophobization reaction, the liquid reaction mixture was neutralized with acetic acid, and the resultant reaction product was collected by filtration. The reaction product was washed twice with 100 g of 80% acetone (containing 20% of water) and then twice with 100 g of acetone, and dried at 70° C. for 24 hours under reduced pressure, thereby obtaining 8.5 g of a hydroxyethyl cellulose derivative (Invention Product 17) substituted by a stearoyl group and a 3-sulfo-2-hydroxypropyl group.

The degrees of substitution by the stearoyl group and the 3-sulfo-2-hydroxypropyl group in the thus-obtained hydroxyethyl cellulose derivative were 0.014 and 0.20, respectively.

EXAMPLE 18

(1) A 1,000-ml glass separable reactor equipped with a stirrer, thermometer and condenser tube was charged with 50 g of hydroxyethyl cellulose (HEC-QP4400, product of Union Carbide Corp.) having a weight average molecular weight of about 800,000 and a degree of substitution by a hydroxyethyl group of 1.8, 400 g of 88% isopropyl alcohol and 3.5 g of a 48% aqueous solution of sodium hydroxide to prepare a slurry. The slurry was stirred at room temperature for 30 minutes in a nitrogen atmosphere. To the slurry, 0.9 g of 1,2-epoxy-n-octadecane were added to conduct a reaction at 80° C. for 8 hours, thereby performing hydrophobization. After completion of the hydrophobization reaction, the liquid reaction mixture was neutralized with acetic acid, and the resultant reaction product was collected by filtration. The reaction product was washed twice with 500 g of 80% acetone and then twice with 500 g of acetone, and dried at 70° C. for 24 hours under reduced pressure, thereby obtaining 48.4 g of hydrophobized hydroxyethyl cellulose derivative.

(2) A 500-ml glass separable reactor equipped with a stirrer, thermometer and condenser tube was charged with 10.0 g of the hydrophobized hydroxyethyl cellulose derivative obtained in the step (1), 80.0 g of isopropyl alcohol and 0.33 g of a 48% aqueous solution of sodium hydroxide to prepare a slurry. The slurry was stirred at room temperature for 30 minutes in a nitrogen atmosphere. A mixture composed of 12.8 g of sodium 3-chloro-2-hydroxypropanesulfonate, 5.4 g of a 48% aqueous solution of sodium hydroxide and 20.0 g of water was added to the resultant liquid reaction mixture to conduct sulfonation at 50° C. for 9 hours. After completion of the reaction, the liquid reaction mixture was neutralized with acetic acid, and the resultant reaction product was collected by filtration. The reaction product was washed 3 times with 500 g of 80% acetone (containing 20% of water) and then twice with 500 g of acetone, and then dried at 70° C. for 24 hours under reduced pressure, thereby obtaining 6.9 g of a hydroxyethyl cellulose derivative (Invention Product 18) substituted by a 2-hydroxy-n-octadecyl group and a sulfo-2-hydroxypropyl group.

The degrees of substitution by the 2-hydroxy-n-octadecyl group and the sulfo-2-hydroxypropyl group in the thus-obtained methyl cellulose derivative were 0.007 and 0.30, respectively.

EXAMPLE 19

A 500-mil glass separable reactor equipped with a stirrer, thermometer and condenser tube was charged with 10.0 g of the hydrophobized methyl cellulose obtained in the step (1) of Example 18, 160 g of isopropyl alcohol and 36.0 g of a 25% aqueous solution of sodium vinylsulfonate to prepare a slurry. After the slurry was stirred at room temperature for 30 minutes in a nitrogen atmosphere, 1.2 g of a 48% aqueous solution of sodium hydroxide were charged, and the resultant slurry mixture was further stirred at room temperature for 60 minutes in a nitrogen atmosphere. The slurry was heated up to 80° C. and stirred at 80° C. for 2 hours to conduct sulfonation. After completion of the reaction, the liquid reaction mixture was cooled down to 60° C. and neutralized with acetic acid, and the resultant reaction product was collected by filtration. The reaction product was washed 3 times with 500 g of 80% acetone (containing 20% of water) and then twice with 500 g of acetone, and then dried at 70° C. for 24 hours under reduced pressure, thereby obtaining 8.5 g of a hydroxyethyl cellulose derivative (Invention Product 19) substituted by a 2-hydroxy-n-octadecyl group and a sulfoethyl group.

The degrees of substitution by the 2-hydroxy-n-octadecyl group and the sulfoethyl group in the thus-obtained hydroxyethyl cellulose derivative were 0.004 and 0.31, respectively.

EXAMPLE 20

A 500-ml glass separable reactor equipped with a stirrer, thermometer and condenser tube was charged with 10.0 g of the hydrophobized hydroxyethyl cellulose obtained in the step (1) of Example 18, 160 g of 90% isopropyl alcohol and 13.1 g of a 48% aqueous solution of sodium hydroxide to prepare a slurry. The slurry was stirred at room temperature for 30 minutes in a nitrogen atmosphere. After the liquid reaction mixture was cooled down to 10° C. or lower with ice water, 30.0 g of sodium 3-bromopropanesulfonate were charged, and the resultant mixture was stirred for 60 minutes at 10° C. or lower. The liquid reaction mixture was heated up to 80° C. and stirred at 80° C. for 2 hours to conduct sulfonation. After completion of the reaction, the liquid reaction mixture was cooled down to 60° C. and neutralized with acetic acid, and the resultant reaction product was collected by filtration. The reaction product was washed 3 times with 500 g of 80% acetone (containing 20% of water) and then twice with 500 g of acetone, and then dried at 70° C. for 24 hours under reduced pressure, thereby obtaining 8.8 g of a hydroxyethyl cellulose derivative (Invention Product 20) substituted by a 2-hydroxy-n-octadecyl group and a sulfopropyl group.

The degrees of substitution by the 2-hydroxy-n-octadecyl group and the sulfopropyl group in the thus-obtained hydroxyethyl cellulose derivative were 0.004 and 0.20, respectively.

Comparative Example 1

Hydrophobization was conducted in the same manner as in Example 1 except that 4.5 g of octylglycidyl ether were used in place of 5.4 g of stearylglycidyl ether, and sulfonation was then performed in the same manner as in Example 3, thereby obtaining a hydroxyethyl cellulose derivative (Comparative Product 1) having an octylglyceryl ether group and a sulfoethyl group.

The degrees of substitution by the octylglyceryl ether group and the sulfoethyl group in the thus-obtained hydroxyethyl cellulose derivative were 0.032 and 0.18, respectively.

Comparative Example 2

The hydroxyethyl cellulose derivative synthesized in the step (1) of Example 1 and substituted by a stearylglyceryl ether group (degree of substitution by the stearylglyceryl ether group: 0.030) was used as Comparative Product 2 as it is.

Comparative Example 3

The same hydroxyethyl cellulose as those used in Examples 1–6 was sulfonated in the same manner as in Example 3 without conducting hydrophobization, thereby obtaining a hydroxyethyl cellulose derivative (Comparative Product 3) substituted by a sulfoethyl group (degree of substitution by the sulfoethyl group: 0.18).

Comparative Example 4

The same hydroxyethyl cellulose (HEC-QP4400, product of Union Carbide Corp.) as those used in Examples 1–6 was used as Comparative Product 4 as it is.

Comparative Example 5

The same hydroxyethyl cellulose (HEC-QP100M, product of Union Carbide Corp.) as those used in Examples 11–16 was used as Comparative Product 5 as it is.

Comparative Example 6

Carboxymethyl cellulose (CMC2280, product of Daicel Chemical Industries, Ltd.; weight average molecular weight: about 1,000,000; degree of carboxymethylation: 0.78) was used as Comparative Product 6 as it is.

Comparative Example 7

Sodium polyacrylate (Carbopol 941, product of Goodrich Co.) was used as Comparative Product 7.

Test Example 1: Test of thickening ability

Each 1.0 g of the invention products and the comparative products were separately dissolved in 200 ml of ion-exchanged water under stirring. After left over for 24 hours at room temperature, the viscosity of each of the aqueous solutions was measured. Besides, each 1.0 g of the invention products and the comparative products were separately dissolved in 200 ml of a 1.0 wt. % aqueous solution of calcium chloride under stirring. After left over for 24 hours at room temperature, the viscosity of each of the aqueous solutions was measured. Incidentally, the viscosity was measured by means of a Brookfield viscometer (12 rpm, 25° C.). The results thereof are shown in Table 1.

TABLE 1

| | Viscosity of 0.5% aq. solution (cps) | |
|---|---|---|
| | Water | 1% CaCl$_2$ |
| Inv. Product 1 | 8,750 | 6,850 |
| Inv. Product 2 | 11,200 | 8,400 |
| Inv. Product 3 | 9,450 | 6,900 |
| Inv. Product 4 | 12,500 | 9,750 |
| Inv. Product 5 | 7,250 | 5,800 |
| Inv. Product 6 | 5,800 | 4,930 |
| Inv. Product 7 | 6,550 | 5,310 |
| Inv. Product 8 | 7,400 | 5,920 |
| Inv. Product 9 | 4,200 | 3,570 |
| Inv. Product 10 | 7,500 | 6,350 |
| Inv. Product 11 | 7,200 | 7,000 |
| Inv. Product 12 | 4,000 | 6,200 |
| Inv. Product 13 | 18,500 | 16,750 |
| Inv. Product 14 | 18,250 | 16,000 |
| Inv. Product 15 | 11,150 | 15,500 |
| Inv. Product 16 | 19,000 | 16,250 |
| Inv. Product 17 | 17,750 | 17,250 |
| Inv. Product 18 | 5,000 | 7,900 |
| Inv. Product 19 | 5,500 | 6,800 |
| Inv. Product 20 | 16,500 | 12,000 |
| Comp. Product 1 | 1,250 | 880 |
| Comp. Product 2 | 10* | 10* |
| Comp. Product 3 | 280 | 200 |
| Comp. Product 4 | 50 | 40 |
| Comp. Product 5 | 50 | 40 |
| Comp. Product 6 | 2,750 | 400 |
| Comp. Product 7 | 12,000 | 20 |

*: Not dissolved.

The novel polysaccharide derivatives according to the present invention permit the provision of an aqueous solution high in transparency, and as apparent from Table 1, exhibit excellent thickening ability and are also excellent in stability to coexistence with the salt.

Test Example 2: Test of emulsion stabilization

An emulsion having the following composition was prepared to visually evaluate its emulsion stability right after the preparation of the emulsion and after stored at 50° C. for 1 week and 2 weeks. Incidentally, each test sample was ranked as A where the emulsion remained uniform, or B where the emulsion separated. The results are shown in Table 2.

<Composition of emulsion>

| | |
|---|---|
| Vaseline | 50.0 wt. % |
| Lanolin | 8.0 wt. % |
| Polyoxyethylene (5EO) lauryl ether | 0.5 wt. % |
| Invention or comparative product | 0.2 wt. % |
| Water | Balance. |

As apparent from Table 2, the polysaccharide derivatives according to the present invention have excellent emulsion stabilizing ability.

Test Example 3: Test of foam stabilization

A solution for testing foam stabilization having the following composition was prepared to evaluate each of the polysaccharide derivatives as to foam stabilizing ability. Incidentally, the volume of foam generated was measured at 40° C. in accordance with the Ross-Miles method after 10 seconds and 120 seconds from the generation of foam. The results are shown in Table 2.

<Solution for testing foam stabilization>

| | |
|---|---|
| Sodium lauryl ether sulfate | 1.0 wt. % |
| Lanolin | 0.5 wt. % |
| Invention or comparative product | 0.1 wt. % |
| Water (hardness: 4°) | Balance. |

TABLE 2

| | Emulsion stabilizing ability (50° C.) | | | Volume of foam generated (ml) | |
|---|---|---|---|---|---|
| | Right after emulsified | After 1 wk. | After 2 wk. | After 10 sec. | After 120 sec. |
| Invention Product 1 | A | A | A | 201 | 189 |
| Invention Product 2 | A | A | A | 210 | 195 |
| Invention Product 3 | A | A | A | 193 | 185 |
| Invention Product 4 | A | A | A | 217 | 204 |
| Invention Product 5 | A | A | A | 194 | 190 |
| Invention Product 6 | A | A | A | 186 | 178 |
| Invention Product 7 | A | A | A | 195 | 186 |
| Invention Product 8 | A | A | A | 183 | 175 |
| Invention Product 9 | A | A | A | 195 | 188 |
| Invention Product 10 | A | A | A | 213 | 201 |
| Invention Product 11 | A | A | A | 205 | 197 |
| Invention Product 12 | A | A | A | 199 | 184 |
| Invention Product 13 | A | A | A | 203 | 199 |
| Invention Product 14 | A | A | A | 210 | 201 |
| Invention Product 15 | A | A | A | 198 | 195 |
| Invention Product 16 | A | A | A | 192 | 185 |
| Invention Product 17 | A | A | A | 199 | 188 |
| Invention Product 18 | A | A | A | 203 | 192 |
| Invention Product 19 | A | A | A | 197 | 181 |
| Invention Product 20 | A | A | A | 200 | 191 |
| Comp. Product 1 | A | A | B | 175 | 163 |
| Comp. Product 2 | A | B | B | 170 | 143 |
| Comp. Product 3 | A | B | B | 170 | 158 |
| Comp. Product 4 | A | B | B | 166 | 140 |
| Comp. Product 5 | A | B | B | 166 | 140 |
| Comp. Product 6 | A | A | B | 165 | 143 |
| Comp. Product 7 | A | A | B | 168 | 142 |
| Blank | A | B | B | 158 | 142 |

As apparent from Table 2, the polysaccharide derivative according to the present invention have excellent foam stabilizing ability and foam increasing ability.

EXAMPLE 21

Cosmetic Emulsion

Invention Cosmetic Emulsion 1 and Comparative Cosmetic Emulsion 1 each having the following composition were prepared to compare them as to viscosity, emulsion stability and feeling upon use. Incidentally, the emulsion stability was evaluated by visually observing the state of each cosmetic emulsion right after its preparation and after stored at 50° C. for 1 week and 1 month. The feeling upon use was evaluated by comparing both cosmetic emulsions by an organoleptic test conducted by 10 expert panelists and expressed in terms of the number of panelists who judged that one sample was superior to the other. The results are shown in Table 3.

<Invention Cosmetic Emulsion 1 (Comparative Cosmetic Emulsion 1)>

| | |
|---|---|
| Invention Product 4 (or Comparative Product 1) | 0.6 wt. % |
| Squalane | 3.0 wt. % |
| Methylcyclopolysiloxane | 12.0 wt. % |
| Methylpolysiloxane | 1.0 wt. % |
| 2-Ethylhexyl p-methoxycinnamate | 5.0 wt. % |
| Silicone-coated zinc oxide | 3.0 wt. % |
| Glycerol | 2.0 wt. % |
| Water | Balance. |

TABLE 3

| | Thickener | Visc. (cps) (25° C.) | Emulsion stability | | | Feeling upon use |
|---|---|---|---|---|---|---|
| | | | Right after | After 1 wk. | After 1 mo. | |
| Invention Cosmetic Emulsion 1 | Invention Product 1 | 14,000 | Even | Even | Even | 8/10 |
| Comp. Cosmetic Emulsion 1 | Comp. Product 1 | 500 | Even | *1 | *2 | 2/10 |

*1: Zinc oxide precipitated.
*2: Separation occurred.

EXAMPLE 22

Cosmetic Emulsion

Invention Cosmetic Emulsion 2 and Comparative Cosmetic Emulsion 2 each having the following composition were prepared to compare them as to viscosity, emulsion stability and feeling upon use. Incidentally, the emulsion stability was evaluated by visually observing the state of each cosmetic emulsion right after its preparation and after stored at 50° C. for 1 week and 1 month. The feeling upon use was evaluated by comparing both cosmetic emulsions by an organoleptic test conducted by 10 expert panelists and expressed in terms of the number of panelists who judged that one sample was superior to the other. The results are shown in Table 4.

<Invention Cosmetic Emulsion 2 (Comparative Cosmetic Emulsion 2)>

| | |
|---|---|
| Invention Product 6 (or Comparative Product 6) | 0.25 wt. % |
| Water (or 53.3 wt. % water + 0.25 wt. % L-arginine) | 53.55 wt. % |
| Ethanol (55 v/v %) | 10.0 wt. % |
| Glycerol | 2.0 wt. % |
| 2-Ethylhexyl p-methoxycinnamate | 3.0 wt. % |
| Methylpolysiloxane | 5.0 wt. % |
| Methylcyclopolysiloxane | 25.0 wt. % |
| Zinc sulfocarbolate | 0.2 wt. % |

-continued

| | |
|---|---|
| Self-emulsifying glycerol monostearate | 0.7 wt. % |
| Sorbitan monostearate | 0.3 wt. %. |

TABLE 4

| | | Visc. | Emulsion stability | | | |
|---|---|---|---|---|---|---|
| | Thickener | (cps) (25° C.) | Right after | After 1 wk. | After 1 mo. | Feeling upon use |
| Invention Cosmetic Emulsion 2 | Invention Product 6 | 15,000 | Even | Even | Even | 9/10 |
| Comp. Cosmetic Emulsion 2 | Comp. Product 6 | ≦500 | *1 | *2 | *2 | 1/10 |

*1: Separation somewhat occurred.
*2: Separation occurred.

EXAMPLE 23

Cosmetic Emulsion

Invention Cosmetic Emulsion 3 and Comparative Cosmetic Emulsion 3 each having the following composition were prepared to compare them as to viscosity, emulsion stability and feeling upon use. Incidentally, the emulsion stability was evaluated by visually observing the state of each cosmetic emulsion right after its preparation and after stored at 50° C. for 1 week and 1 month. The feeling upon use was evaluated by comparing both cosmetic emulsions by an organoleptic test conducted by 10 expert panelists and expressed in terms of the number of panelists who judged that one sample was superior to the other. The results are shown in Table 5.

<Invention Cosmetic Emulsion 3 (Comparative Cosmetic Emulsion 3)>

| | |
|---|---|
| Invention Product 13 (or Comparative Product 6) | 0.5 wt. % |
| Squalane | 3.0 wt. % |
| Methylcyclopolysiloxane | 15.0 wt. % |
| Methylpolysiloxane | 1.0 wt. % |
| Glycerol | 3.0 wt. % |
| Water | Balance. |

TABLE 5

| | | Visc. | Emulsion stability | | | |
|---|---|---|---|---|---|---|
| | Thickener | (cps) (25° C.) | Right after | After 1 wk. | After 1 mo. | Feeling upon use |
| Invention Cosmetic Emulsion 3 | Invention Product 13 | 25,000 | Even | Even | Even | 9/10 |
| Comp. Cosmetic Emulsion 3 | Comp. Product 6 | 800 | Even | *1 | — | 1/10 |

*1: Separation occurred.

EXAMPLE 24

Cosmetic Emulsion

Invention Cosmetic Emulsion 4 and Comparative Cosmetic Emulsion 4 each having the following composition were prepared to compare them as to viscosity, emulsion stability and feeling upon use. Incidentally, the emulsion stability was evaluated by visually observing the state of each cosmetic emulsion right after its preparation and after stored at 50° C. for 1 week and 1 month. The feeling upon use was evaluated by comparing both cosmetic emulsions by an organoleptic test conducted by 10 expert panelists and expressed in terms of the number of panelists who judged that one sample was superior to the other. The results are shown in Table 6.

<Invention Cosmetic Emulsion 4 (Comparative Cosmetic Emulsion 4)>

| | |
|---|---|
| Invention Product 14 (or Comparative Product 7) | 0.6 wt. % |
| Squalane | 3.0 wt. % |
| Methylcyclopolysiloxane | 12.0 wt. % |
| Methylpolysiloxane | 1.0 wt. % |
| 2-Ethylhexyl p-methoxycinnamate | 5.0 wt. % |
| Silicone-coated zinc oxide | 3.0 wt. % |
| Glycerol | 2.0 wt. % |
| Water | Balance. |

TABLE 6

| | | Visc. | Emulsion stability | | | |
|---|---|---|---|---|---|---|
| | Thickener | (cps) (25° C.) | Right after | After 1 wk. | After 1 mo. | Feeling upon use |
| Invention Cosmetic Emulsion 4 | Invention Product 14 | 20,250 | Even | Even | Even | 10/10 |
| Comp. Cosmetic Emulsion 4 | Comp. Product 7 | 400 | *1 | — | — | 0/10 |

*1: Zinc oxide precipitated.

EXAMPLE 25

Toilet Water

A toilet water was prepared in accordance with the following formulation. This toilet water was excellent in stability and also good in feeling upon use without being sticky to the touch.

| | |
|---|---|
| Ethanol | 30.0 wt. % |
| Glycerol | 5.0 wt. % |
| Polyethylene glycol 1500 | 4.0 wt. % |
| Polyoxyethylene (20 EO) oleyl ether | 0.5 wt. % |
| Polyoxyethylene (30 EO) hardened castor oil | 0.5 wt. % |
| One of Invention Products 1–20 | 0.2 wt. % |
| Water | Balance. |

EXAMPLE 26

Cosmetic Emulsion

A cosmetic emulsion was prepared in accordance with the following formulation. This cosmetic emulsion was excellent in stability and also good in feeling upon use without being sticky to the touch.

| | |
|---|---|
| Squalane | 5.0 wt. % |
| Olive oil | 8.0 wt. % |

-continued

| | |
|---|---|
| Jojoba oil | 1.0 wt. % |
| Polyoxyethylene (10 EO) hardened castor oil | 1.0 wt. % |
| Sorbitan monostearate | 1.0 wt. % |
| One of Invention Products 1–20 | 0.5 wt. % |
| Butylparaben | 0.1 wt. % |
| Methylparaben | 0.1 wt. % |
| Ethanol | 5.0 wt. % |
| Glycerol | 3.0 wt. % |
| Perfume base | 0.05 wt. % |
| Water | Balance. |

EXAMPLE 27

Toilet Water

A toilet water was prepared in accordance with the following formulation. This toilet water was stable even after stored at 50° C. for 1 month, and also good in feeling upon use.

| | |
|---|---|
| Ethanol | 5.0 wt. % |
| Glycerol | 3.0 wt. % |
| Polyethylene glycol 1500 | 4.0 wt. % |
| Polyoxyethylene (20 EO) oleyl ether | 0.3 wt. % |
| Polyoxyethylene (30 EO) hardened castor oil | 0.2 wt. % |
| One of Invention Products 1–20 | 0.15 wt. % |
| Zinc p-phenolsulfonate | 0.2 wt. % |
| Water | Balance. |

EXAMPLE 28

Sunscreen skin-care cream

A sunscreen skin-care cream was prepared in accordance with the following formulation. This sunscreen skin-care cream was stable even after stored at 50° C. for at least 1 month, and also good in feeling upon use.

| | |
|---|---|
| Dimethylsiloxane-methyl (polyoxyethylene) - siloxane copolymer | 2.0 wt. % |
| Polyoxyethylene (20 EO) sorbitan monooleate | 0.5 wt. % |
| Methylpolysiloxane (5 cs) | 7.0 wt. % |
| Jojoba oil | 2.0 wt. % |
| Dextrin palmitate | 0.5 wt. % |
| Octyldimethyl PABA | 4.0 wt. % |
| Finely particulate titanium oxide coated with silicone | 5.0 wt. % |
| Acid heteropolysaccharide | 0.03 wt. % |
| Magnesium sulfate | 0.5 wt. % |
| Glycerol | 5.0 wt. % |
| Dibutylhydroxytoluene | 0.05 wt. % |
| One of Invention Products 1–20 | 0.5 wt. % |
| Water | Balance. |

EXAMPLE 29

Foundation

A foundation was prepared in accordance with the following formulation. This foundation was stable even after stored at 50° C. for at least 1 month, and also good in feeling upon use.

| | |
|---|---|
| One of Invention Products 1–20 | 0.2 wt. % |
| α-Monoisostearylglyceryl ether | 2.0 wt. % |
| Aluminum diisostearate | 0.2 wt. % |
| Liquid paraffin | 10.0 wt. % |
| Neopentyl glycol dioctanoate | 5.0 wt. % |
| Methylphenylpolysiloxane (14 cs) | 5.0 wt. % |
| 2-Ethylhexyl p-methoxycinnamate | 3.0 wt. % |
| 2-Hydroxy-4-methoxybenzophenone | 1.0 wt. % |
| Finely particulate titanium oxide coated with silicone | 5.0 wt. % |
| Finely particulate zinc oxide coated with silicone | 1.0 wt. % |
| Sericite | 2.0 wt. % |
| Talc | 2.0 wt. % |
| Iron oxide red | 0.4 wt. % |
| Iron oxide yellow | 0.7 wt. % |
| Black iron oxide | 0.7 wt. % |
| Magnesium sulfate | 1.0 wt. % |
| Methylparaben | 0.2 wt. % |
| Perfume base | Trace amount |
| Water | Balance. |

EXAMPLE 30

Lipstick

A lipstick was prepared in accordance with the following formulation. This lipstick was stable even after stored at 50° C. for at least 1 month, and also good in feeling upon use.

| | |
|---|---|
| Castor oil | 52.0 wt. % |
| Lanolin | 5.0 wt. % |
| Liquid lanolin | 5.0 wt. % |
| Beeswax | 4.0 wt. % |
| Ozocerite | 7.0 wt. % |
| Candelilla wax | 2.0 wt. % |
| Carnauba wax | 1.0 wt. % |
| Dodecyl-modified silicone | 10.0 wt. % |
| One of Invention Products 1–20 | 0.2 wt. % |
| Momomenthyl salicylate | 7.8 wt. % |
| Titanium oxide | 1.0 wt. % |
| Red Color No. 201 | 1.0 wt. % |
| Red Color No. 202 | 2.0 wt. % |
| Yellow Color No. 4 aluminum lake | 1.0 wt. % |
| Red Color No. 223 | 0.1 wt. % |
| Perfume base | Trace amount |
| Butylated hydroxytoluene | 0.1 wt. % |
| Propylparaben | 0.3 wt. %. |

What is claimed is:

1. A polysaccharide derivative obtained by substituting a part or the whole of hydrogen atoms of hydroxyl groups in a polysaccharide or a derivative thereof by the following substituents (A) and (B):

(A) a hydrophobic group having a linear or branched alkyl, alkenyl or acyl group having 10–40 carbon atoms; and (B) a sulfoalkyl group having 1–5 carbon atoms, which may be substituted by a hydroxyl group, or a salt thereof, wherein an average degree of substitution by the substituent (A) per monosaccharide residue is 0.00–1.0, and an average degree of substitution by the substituent (B) per monosaccharide residue is 0.01–2.0, wherein either (1) the substitution by substituent (A) is conducted before the substitution by substituent (B), or (2) the substitution by substituent (B) is conducted before the substitution by substituent (A), or (3) the substitution by substituent A and the substitution by substituent B are conducted simultaneously.

2. The polysaccharide derivative according to claim 1, wherein the substituent (A) is a linear or branched alkyl, alkenyl or acyl group having 10–40 carbon atoms which may be substituted by a hydroxyl group or which may be substituted by an oxycarbonyl group (—COO— or —OCO—), an alkylglyceryl ether group having a linear or branched alkyl group having 10–40 carbon atoms, or an alkenylglyceryl ether group having a linear or branched alkenyl group having 10–40 carbon atoms.

3. The polysaccharide derivative according to claim 1, wherein the substituent (A) is an alkylglyceryl ether group having a linear or branched alkyl group having 10–40 carbon atoms, or an alkenylglyceryl ether group having a linear or branched alkenyl group having 10–40 carbon atoms.

4. The polysaccharide derivative according to claim 1, wherein the substituent (A) is an alkylglyceryl ether group having a linear or branched alkyl group having 12–36 carbon atoms.

5. The polysaccharide derivative according to claim 1, wherein the polysaccharide or the derivative thereof is selected from the group consisting of cellulose, guar gum, starch, hydroxyethyl cellulose, hydroxyethyl guar gum, hydroxyethyl starch, methyl cellulose, methyl guar gum, methyl starch, ethyl cellulose, ethyl guar gum, ethyl starch, hydroxypropyl cellulose, hydroxypropyl guar gum, hydroxypropyl starch, hydroxyethylmethyl cellulose, hydroxyethylmethyl guar gum, hydroxyethylmethyl starch, hydroxypropylmethyl cellulose, hydroxypropylmethyl guar gum and hydroxypropylmethyl starch.

6. The polysaccharide derivative according to claim 1, wherein the polysaccharide or the derivative thereof is selected from the group consisting of cellulose, hydroxyethyl cellulose, methyl cellulose, ethyl cellulose, hydroxypropyl cellulose, hydroxyethylmethyl cellulose and hydroxypropylmethyl cellulose.

7. A process for preparing a polysaccharide derivative by reacting a polysaccharide or a derivative thereof with (a) a compound selected from the group consisting of glycidyl ethers, epoxides, halides, halohydrins, esters, acid anhydrides and acyl halides each having a hydrophobic group containing a linear or branched alkyl, alkenyl or acyl group having 10–40 carbon atoms which may be substituted by a hydroxyl group or which may be substituted by an oxycarbonyl group (—COO— or —OCO—), and (b) a sulfonating agent selected from the group consisting of vinylsulfonic acid, halogenated $C_{1-5}$ alkanesulfonic acids which may be substituted by a hydroxyl group, and salts thereof, wherein either (1) the reaction with the compound is conducted before the reaction with the sulfonating agent, or (2) the reaction with the sulfonating agent is conducted before the reaction with the compound, or (3) the reaction with the compound and the reaction with the sulfonating agent are conducted simultaneously.

8. A process for thickening cosmetic ingredients, which comprises adding a polysaccharide derivative obtained by substituting a part or the whole of hydrogen atoms of hydroxyl groups in a polysaccharide or a derivative thereof by the following substituents (A) and (B):

(A) a hydrophobic group having a linear or branched alkyl, alkenyl or acyl group having 10–40 carbon atoms; and (B) a sulfoalkyl group having 1–5 carbon atoms, which may be substituted by a hydroxyl group, or a salt thereof, wherein an average degree of substitution by the substituent (A) per monosaccharide residue is 0.001–1.0, and an average degree of substitution by the substituent (B) per monosaccharide residue is 0.01–2.0, to the cosmetic ingredients, wherein either (1) the substitution by substituent (A) is conducted before the substitution by substituent (B), or (2) the substitution by substituent (B) is conducted before the substitution by substituent (A), or (3) the substitution by substituent A and the substitution by substituent B are conducted simultaneously.

9. A cosmetic composition comprising a polysaccharide derivative obtained by substituting a part or the whole of hydrogen atoms of hydroxyl groups in a polysaccharide or a derivative thereof by the following substituents (A) and (B):

(A) a hydrophobic group having a linear or branched alkyl, alkenyl or acyl group having 10–40 carbon atoms; and (B) a sulfoalkyl croup having 1–5 carbon atoms, which may be substituted by a hydroxyl group, or a salt thereof, wherein an average degree of substitution by the substituent (A) per monosaccharide residue is 0.001–1.0, and an average degree of substitution by the substituent (B) per monosaccharide residue is 0.01–2.0, wherein either (1) the substitution by substituent (A) is conducted before the substitution by substituent (B), or (2) the substitution by substituent (B) is conducted before the substitution by substituent (A), or (3) the substitution by substituent A and the substitution by substituent B are conducted simultaneously.

* * * * *

UNITED STATES PATENT AND TRADEMARK OFFICE
CERTIFICATE OF CORRECTION

PATENT NO. : 5,891,450
DATED : April 6, 1999
INVENTOR(S) : Tetsuya Miyajima, et al.

It is certified that error appears in the above-indentified patent and that said Letters Patent is hereby corrected as shown below:

Column 28, Line 56, "0.00-1.0," should read --0.001-1.0,--.

Signed and Sealed this

Twenty-sixth Day of October, 1999

Attest:

Q. TODD DICKINSON

*Attesting Officer*    *Acting Commissioner of Patents and Trademarks*